US009078821B2

(12) United States Patent
Sun et al.

(10) Patent No.: US 9,078,821 B2
(45) Date of Patent: Jul. 14, 2015

(54) METHODS FOR MAKING DENTAL PROSTHESIS BY THREE-DIMENSIONAL PRINTING

(75) Inventors: Benjamin J. Sun, York, PA (US); Andrew M. Lichkus, York, PA (US)

(73) Assignee: DENTSPLY International Inc., York, PA (US)

( * ) Notice: Subject to any disclaimer, the term of this patent is extended or adjusted under 35 U.S.C. 154(b) by 704 days.

(21) Appl. No.: 12/317,467

(22) Filed: Dec. 23, 2008

(65) Prior Publication Data

US 2011/0049738 A1    Mar. 3, 2011

Related U.S. Application Data

(63) Continuation of application No. 10/405,169, filed on Apr. 2, 2003, now Pat. No. 7,476,347, which is a continuation-in-part of application No. 10/106,741, filed on Mar. 26, 2002, now abandoned, which is a continuation-in-part of application No. 09/682,440, filed on Sep. 4, 2001, now Pat. No. 6,592,369, which is a continuation-in-part of application No. 09/670,364, filed on Sep. 26, 2000, now abandoned.

(60) Provisional application No. 60/237,523, filed on Oct. 4, 2000, provisional application No. 60/201,705, filed on May 3, 2000, provisional application No. 60/164,893, filed on Nov. 10, 1999.

(51) Int. Cl.
*A61C 13/00* (2006.01)
*A61K 6/09* (2006.01)

(52) U.S. Cl.
CPC .......................................... *A61K 6/09* (2013.01)

(58) Field of Classification Search
USPC ........................ 264/16, 17, 19, 401, 494, 496
See application file for complete search history.

(56) References Cited

U.S. PATENT DOCUMENTS

| 2,514,075 | A | * | 7/1950 | Kelly ........................ 433/203.1 |
| 5,348,475 | A | * | 9/1994 | Waknine et al. .............. 433/215 |
| 6,057,383 | A | * | 5/2000 | Volkel et al. .................. 523/116 |
| 6,512,994 | B1 | * | 1/2003 | Sachdeva ...................... 702/167 |
| 2002/0127345 | A1 | * | 9/2002 | Rheinberger et al. ......... 427/421 |
| 2002/0167100 | A1 | * | 11/2002 | Moszner et al. ................ 264/16 |

* cited by examiner

Primary Examiner — Larry Thrower
Assistant Examiner — Xue Liu
(74) Attorney, Agent, or Firm — David A. Zdurne; Douglas J. Hura; Leana Levin

(57) ABSTRACT

This invention relates to methods for making a three-dimensional dental prosthesis using ink-jet printing systems. An ink-jet printer is used to discharge light-curable, wax-like polymerizable material in a layer-by-layer manner to build-up the prosthesis. The methods are particularly useful for making integrated dentures containing a set of artificial teeth. The denture base and set of teeth are made of light-curable, wax-like polymerizable materials comprising a mixture of monomer, oligomer, and light sensitizer. The wax-like materials are dimensionally stable in their uncured states. The denture base and artificial teeth are later light-cured to form a polymerized denture product having high flexural modulus and flexural strength.

20 Claims, 7 Drawing Sheets

METHODS FOR MAKING DENTAL PROSTHESIS BY THREE-DIMENSIONAL PRINTING

CROSS-REFERENCE TO RELATED APPLICATIONS

This application is a continuation of and claims the benefit of U.S. patent application Ser. No. 10/405,169 having a filing date of Apr. 2, 2003 now U.S. Pat. No. 7,476,347, which is continuation-in-part of U.S. patent application Ser. No. 10/106,741 filed Mar. 26, 2002, now abandoned, which is a continuation-in-part of U.S. patent application Ser. No. 09/682,440 filed Sep. 4, 2001, now U.S. Pat. No. 6,592,369, which is a continuation-in-part of U.S. patent application Ser. No. 09/670,364 filed Sep. 26, 2000, now abandoned, the entire contents of which are hereby incorporated by reference. The application further claims the benefit of U.S. Provisional Patent Application Ser. No. 60/237,523 filed Oct. 4, 2000; U.S. Provisional Patent Application Ser. No. 60/201,705 filed May 3, 2000, and U.S. Provisional Patent Application Ser. No. 60/164,893 filed Nov. 10, 1999.

DETAILED DESCRIPTION OF THE INVENTION

Figure 1:
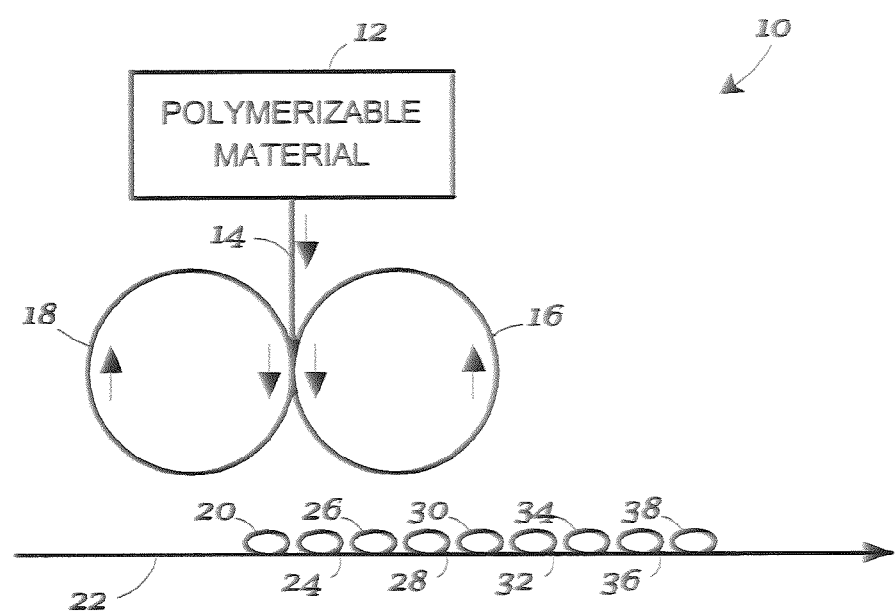
FIG. 1 is a schematic view of a continuous tooth making system in accordance with the invention.

The invention provides integrally connected dental devices. The invention is now described with more particular reference to FIGS. 1 through 7. With more particular reference to FIG. 1 is seen a schematic view of a continuous tooth making system 10 having source of polymerizable material 12 feeding a strip of polymerizable material 14 between rotating molds 16 and 18 to form artificial teeth 20, 24, 26, 28, 30, 32, 34, 36 and 38. The artificial teeth drop onto and are carried by moving belt 22.

Figure 2:
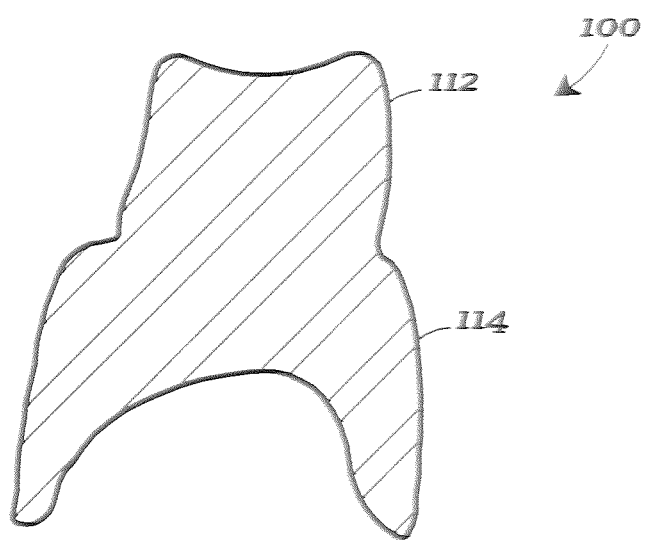
FIG. 2 is a cross-sectional side view of an integral tooth and denture base in accordance with the invention.

With more particular reference to FIG. 2 is seen an integral tooth and denture base 100 having an artificial tooth portion 112 integrally formed with denture base portion 114.

In a preferred embodiment of the invention a polymerizable material 12 made be placed in polymerizable denture base material and light cured to form integral tooth and denture base 100. During polymerization of the polymerizable dental material it is believed that the dental material flows between the artificial tooth and the denture base while polymerizing. Preferably a cross-linked system is formed. After polymerization of the polymerizable dental materials, there is no detectable interface in the region of the integral connection of the artificial tooth to the denture base. In a preferred embodiment of the temperature of the denture base is below temperatures at which the material of the artificial tooth is flowable. Initially there is a detectable interface between the artificial tooth material to the denture base material.

Integral connections, as used herein, refers to adjacent regions of a polymerized product that are flowable while they are polymerized. For example, when heated adjacent regions of a polymerizable artificial tooth (containing monomer and oligomer) and a polymerizable denture base (containing monomer and oligomer) become flowable, and flow while they polymerize. Thus, in the initial stage of polymerization, monomer and oligomer flow from the polymerizable artificial tooth into the adjacent polymerizable denture base. Similarly, monomer and oligomer flow from the polymerizable denture base into the adjacent polymerizable artificial tooth.

The invention provides a dental device, having an artificial tooth and a denture base. The artificial tooth is integrally connected to the denture base. In a preferred embodiment of the invention the artificial tooth is preferably shaped by a continuous molding method. Alternatively the artificial tooth is transfer molded or injection molded. The dental device is formed from polymerizable dental material, which may include one or more initiating systems to cause them to harden promptly.

Thus, as described above in discussing FIG. 2, for a preformed artificial tooth placed into a denture base, if the temperature of the denture base is below temperatures at which the material of the artificial tooth is flowable, then initially there will be a detectable interface between the artificial tooth to the denture base. During polymerization of the polymerizable dental material it is believed that the dental materials flow between the artificial tooth and the denture base. After polymerization of the polymerizable dental material, there is no detectable interface in the region of the integral connection of the artificial tooth to the denture base.

However, if the temperature of the denture base is at or above temperatures at which the material of the artificial tooth is flowable, then initially there will not be a detectable interface between the artificial tooth to the denture base. During polymerization of the polymerizable dental material it is believed that the dental materials flow between the original artificial tooth and the original denture base. After polymerization of the polymerizable dental material, there is no detectable interface in the region of the integral connection of the artificial tooth to the denture base. In the dental device the artificial tooth is integrally connected to the denture base. The dental device is preferably formed from an artificial tooth having tooth material and a submerged tooth surface. A portion of the tooth material flows through the submerged surface into the adjacent denture base. The adjacent denture base includes denture base material. A portion of the denture base material flows through the submerged surface of the artificial tooth whereby the submerged surface of the tooth is assimilated into the tooth material and the adjacent denture base material to form an integral connection between the artificial tooth and the denture base. The flow of tooth and denture base materials typically occurs during polymerization. When polymerization is complete cross-sections of an artificial tooth integrally connected to a denture base at the position of the pre-flowing tooth surface and the adjacent pre-flowing denture base are without a detectable residue of the pre-flowing tooth surface contacting the denture base material. When polymerization is complete cross-sections of an artificial tooth integrally connected to a denture base at the position of the pre-flowing tooth surface and the adjacent pre-flowing denture base have flexural strength and flexural modulus which are each effectively an average of the flexural strength and flexural modulus of the adjacent materials.

Light curable polymerizable dental materials preferably include a light sensitizer, for example camphorquinone, Lucirin TPO, or methyl benzoin which causes polymerization to be initiated upon exposure to activating wavelengths of light; and/or a reducing compound, for example tertiary amine. A room temperature or heat activating catalyst system is preferably included in the polymerizable dental material. For example a peroxide capable of producing free radicals when activated by a reducing agent at room temperature or by heating. Preferred peroxides include benzyl peroxide and lauroyl peroxide.

Compositions useful in accordance with the invention may further include fillers, pigments, stabilizers, plasticizers and fibers. Preferably, these polymerizable dental compositions include from about 2 to about 95 percent by weight filler particles. More preferably, these compositions include from about 10 to about 85 percent by weight filler. Nanocomposites and ceramers may be formed from these composites. The fillers preferably include both organic and inorganic particulate fillers to further reduce polymerization shrinkage, improve wear resistance and modify the mechanical and physical properties.

A preferred embodiment of the invention uses a high strength dental polymeric material formed by light curing polymerizable dental material shaped into at least a portion of a denture base or tooth. Preferably the polymerizable dental material has a flexural modulus of at least 250,000 psi and a flexural strength of at least 7,000 psi. Preferably a denture of the invention comprises a denture base and a tooth integrally connected and comprising an interpenetrating polymer network polymeric matrix and at least 0.1 percent by weight of self-lubricating particles having a particle size less than 500 microns effectively bonded to and distributed in the polymeric matrix. Preferably the integral connection of the denture base and a tooth is effectively greater than a bond strength of 4,480 psi.

"Wax-like material" as used herein refers to material which is flowable (fluid) above 40° C. and becomes dimensionally stable (solidifies: i.e. is nonfluid) at least at and below 23° C., within 5 minutes. Thus, wax-like material is flowable when it is at and above 40° C., and becomes dimensionally stable when it is at and below 23° C. Flowable wax-like material having a temperature from 100° C. to 40° C., becomes dimensionally stable within 5 minutes by exposure to an ambient temperature between 23° C. and 0° C. Flowable wax-like material having a temperature from 100° C. to 40.° C., becomes dimensionally stable within (in order of increasing preference) 2, 1, 0.5 or 0.3 minutes by cooling by exposure to an ambient temperature between 23° C. and 0° C.

"Wax-like spray material" as used herein refers to material which is fluid at temperatures of fluidity of the wax-like spray material, and dimensionally stable (solidifies: i.e. is nonfluid) at temperatures of dimensional stability of the wax-like spray material, which is adapted to be spayed as a fluid, and adapted to solidify from a fluid spray to being dimensionally stable within 5 minutes of the fluid spray contacting a substrate which is at temperatures of dimensionally stability of the wax-like spray material. Preferably, wax-like spray material (in order of increasing preference) is flowable (fluid) within the range of 1° C. to 100° C.; 2° C. to 80° C.; 4° C. to 60° C.; or 5° C. to 50° C. above the highest temperature of the temperatures of dimensionally stability of the wax-like spray material. Preferably, wax-like spray material becomes dimensionally stable within (in order of increasing preference) 2, 1, 0.5, 0.3 or 0.1 minute(s) by cooling by contacting a substrate at temperatures of dimensionally stability of the wax-like spray material. Preferably, a dental product is formed from wax-like spray material within an enclosure at an average ambient temperature within the enclosure between 0° C. and 80° C. More preferably, the average ambient temperature within the enclosure is between 15° C. and 50° C. Most preferably, the average ambient temperature within the enclosure is between 20° C. and 40° C.

"High strength dental polymeric material" as used herein refers to material having a polymeric matrix having a flexural modulus of at least 250,000 psi and a flexural strength of at least 5,000 psi. Optionally, high strength dental polymeric material includes reinforcing filler. However, the polymeric matrix alone (without any reinforcing filler) has a flexural modulus of at least 250,000 psi and a flexural strength of at least 5,000 psi. Preferably high strength dental polymeric material has a polymeric matrix having a flexural modulus of at least 300,000 psi and a flexural strength of at least 7,000 psi. More preferably high strength dental polymeric material in order of increasing preference has a polymeric matrix having a flexural modulus of at least 350,000 psi and a flexural strength of at least 12,000 psi. Artificial teeth and denture base both made of high strength dental polymeric material are integrally connected in dental products including full dentures, partial dentures and bridges during polymerization of polymerizable dental material.

"Flexural strength, and flexural modulus" as used herein refers to results of testing according to ASTM D790 (1997). "Notched impact strength" as used herein is also referred to as "notched Izod impact resistance" and refers to results of testing according to ASTM D256 (1997). "Un-notched impact strength" as used herein refers to results of testing according to ASTM D4812 (1993).

Integral dental devices in accordance with a preferred embodiment of the invention have at least one artificial tooth integrally connected to the denture base, and are formed of high strength dental polymeric material. The integral connection of each artificial tooth to the denture base provides superior strength in joining artificial teeth to denture base compared to prior art dental devices. The integral connection of each artificial tooth to the denture base eliminates the need for a coating of a bonding agent there between in prior art dental devices. The integral connection of each artificial tooth to the denture base provides superior sealing at the margins (outer surfaces) in joining artificial teeth to denture base compared to prior art dental devices.

Figure 3:
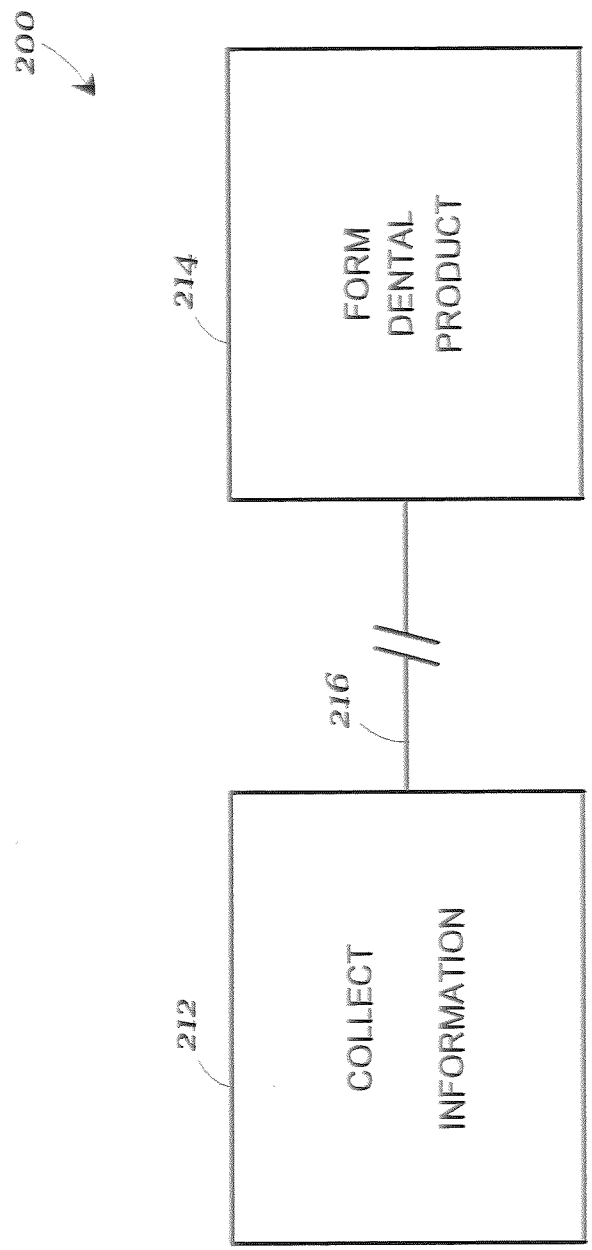
FIG. 3 is a schematic representation of an information collection, denture forming and information transmission system in accordance with the invention.

With more particular reference to FIG. 3 is seen system 200 having information collection 212 and dental product forming 214 with information transmission 216 from information collection 212 to dental product forming 214. Information collection 212 provides three-dimensional digital information representative of a portion of a patient's mouth. Information collection 212 may for example be the apparatus for producing a three-dimensional digital model disclosed by Sachdeva in U.S. Pat. No. 6,512,994, incorporated herein by reference in its entirety. Alternatively, Information collection 212 may be the impression tray scanning apparatus disclosed by Hultgren in U.S. Pat. No. 6,2000,135, incorporated herein by reference in its entirety.

Digital information or data representative of a tooth enamel and shader outer surfaces are prepared, for example as disclosed in U.S. Pat. No. 6,174,168 (incorporated herein by reference in its entirety) or retrieved from memory of a computer loaded with CAD/CAM software program. This data and three-dimensional digital information from information collection 212 representative of a portion of a patient's mouth, which may both be in the form of the numerical coordinates of a spray path program, are collected by a memory device and may be down loaded or transferred to a floppy disk. The spray path program may be used to display and edit features of the dental product to be formed. The edited spray path program may be stored on a floppy disk and down loaded into the memory (such as a digital storage unit) of control system 330 of dental product making system 300. The spray path program is used to direct and control the machine in the fabrication of the dental product. The spray path program forms the lower surface of the dental product using the three-dimensional digital information from information collection 212 representative of a portion of a patient's mouth. The spray path program forms the upper outer surface of the dental product using the digital information representative of tooth enamel outer surfaces.

Information transmission 216 may be in digital form, and carried for example on diskette or transferred via a telephone system, such as the internet. Dental product forming 214 may, for example, be by liquid jet deposition of pigmented photopolymerizable (light curable) material. Information collection 212 may, for example, be by scanning a patient's mouth or scanning a mold (or an impression) of a patient's mouth. Preferably, information collection 212 provides information about a patient's mouth in machine readable form.

In accordance with a preferred embodiment of the invention is provided a denture made by a process comprising: collecting digital information regarding a mouth, and forming a denture using the information. Preferably the forming of the denture comprises computer aided manufacture. The collecting digital information regarding a mouth is preferably by scanning at least a portion of the mouth or by taking an impression of at least a portion of the mouth and scanning the impression. The denture is formed using the information at the same or at a location remote to the collecting of digital information regarding a mouth. Thus, the invention provides a denture made by a process comprising: collecting digital information regarding a mouth at a first location, and forming a denture using the information at a second location. Preferably the process further comprises transferring the digital information from the first location to the second location through a telephone system. Preferably the process further comprises storing the digital information on a disk and transferring the disk from the first location to the second location.

Figure 4:
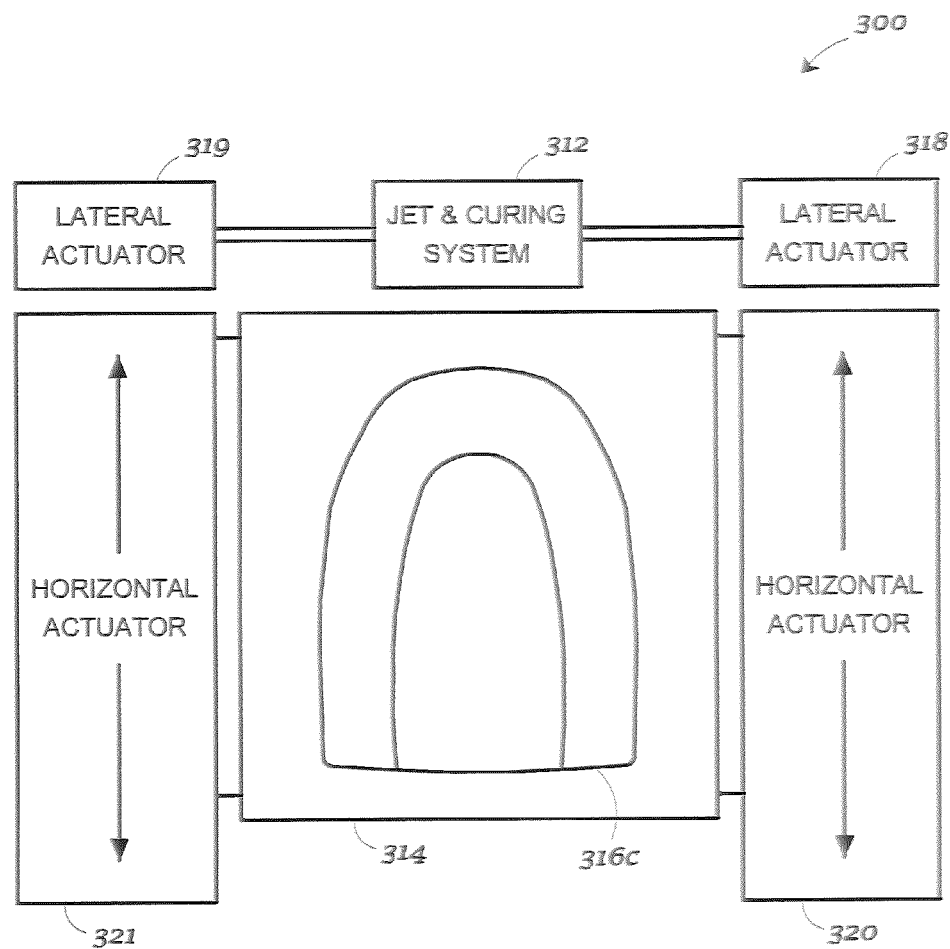
FIG. 4 is a top view a schematic representation of device making system in accordance with the invention.
Figure 5:
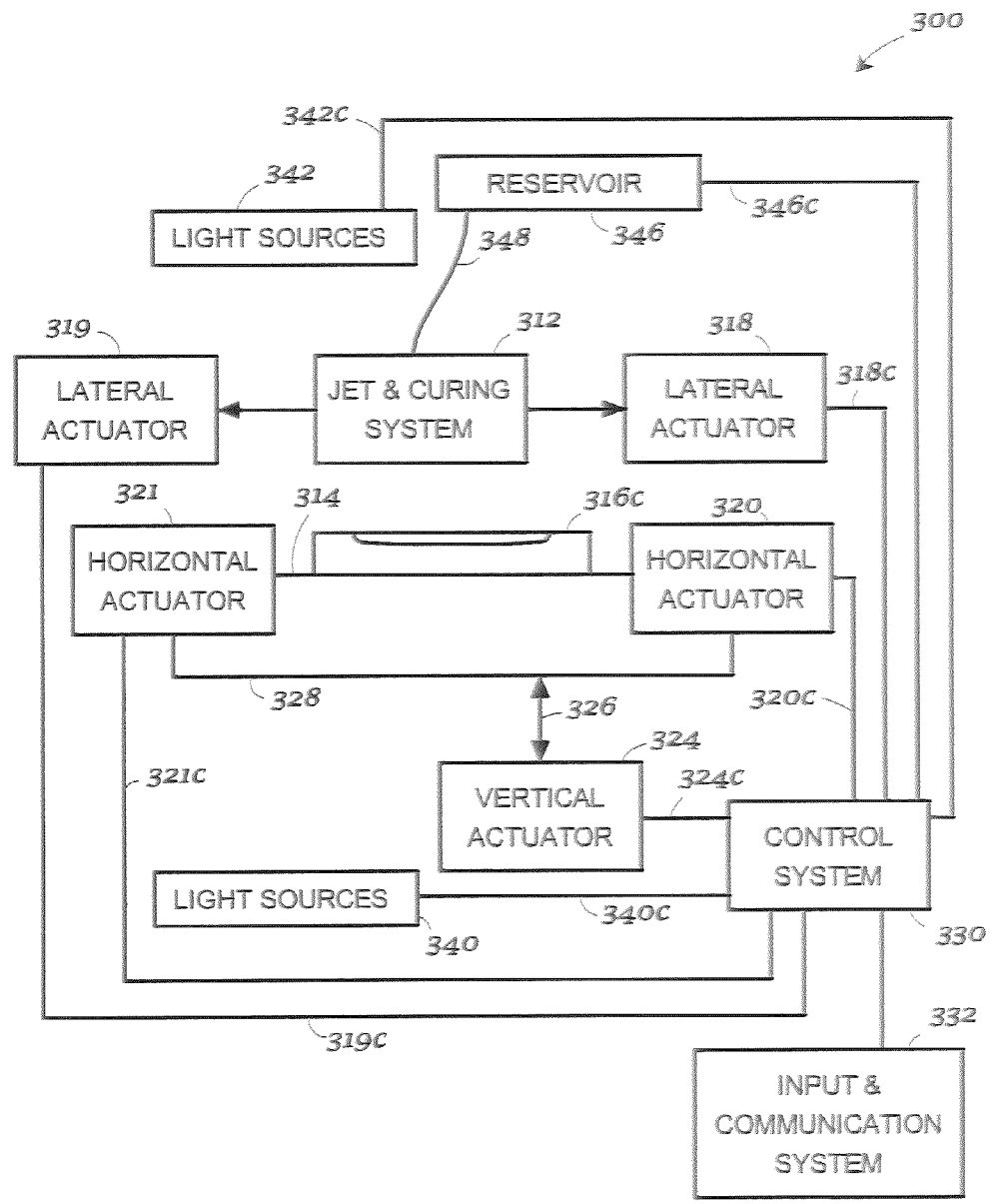
FIG. 5 is a side view a schematic representation of the device making system shown in FIG. 4.

With more particular reference to FIGS. 4 and 5 is seen dental product making system 300 having jet and curing system 312 above support surface 314. A denture layer 316C is formed by spraying and curing the polymerizable material from jet and curing system 312 onto support surface 314. Jet and curing system 312 is incrementally moved in a plane above support surface 314 by horizontal actuators 320 and 321. For each increment jet and curing system 312 is moved in a plane above support surface 314 jet and curing system 312 is moved laterally across at least a portion of support surface 314 by lateral actuators 318 and 319.

Vertical actuator 324 is connected by actuator 326 to frame 328. Frame 328 is connected to support surface 314 and horizontal actuators 320 and 321. After jet and curing system 312 is incrementally moved through at least a portion of a plane above support surface 314 by horizontal actuators 320 and 321, vertical actuator 324 lowers support surface 314 and horizontal actuators 320 and 321 a distance corresponding to the height of the added layer of polymerizable material sprayed and polymerized.

Control system 330 received information from input and communication system 332. Control system 330 is connected to horizontal actuators 320 and 321, lateral actuators 318 and 319 and vertical actuator 324 through horizontal actuator electrical conductors 320C and 321C, lateral actuator electrical conductors 318C and 319C and vertical actuator electrical conductor 324C, respectively. Control system 330 controls actuator movement of horizontal actuators 320 and 321, lateral actuators 318 and 319 and vertical actuator 324.

Control system 330 is connected to light sources 340 and 342 through light sources electrical conductors 340C and 342C. Control system 330 controls the emission of curing light from light sources 340 and 342.

Figure 6:
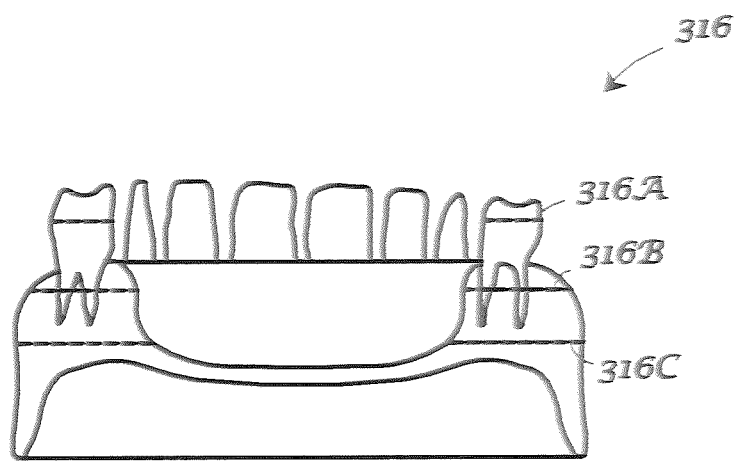
FIG. 6 is a cross-sectional end view schematic representation of a denture made in the device making system shown in FIGS. 4 and 5.

Control system 330 is connected through control valve electrical conductor 346C to control valve for reservoir 346. Control system 330 controls the flow of fluid from reservoir 346 by opening and closing of a valve reservoir 346. Fluid flowing from reservoir 346 sprays onto denture layer 316C. Denture forming fluid from reservoir 346 is light curable polymerizable material. With more particular reference to FIG. 6 is seen denture 316 having a denture base and artificial teeth formed on surface 314 in integrally connected layers 316A, 316B and 316C.

Figure 7:
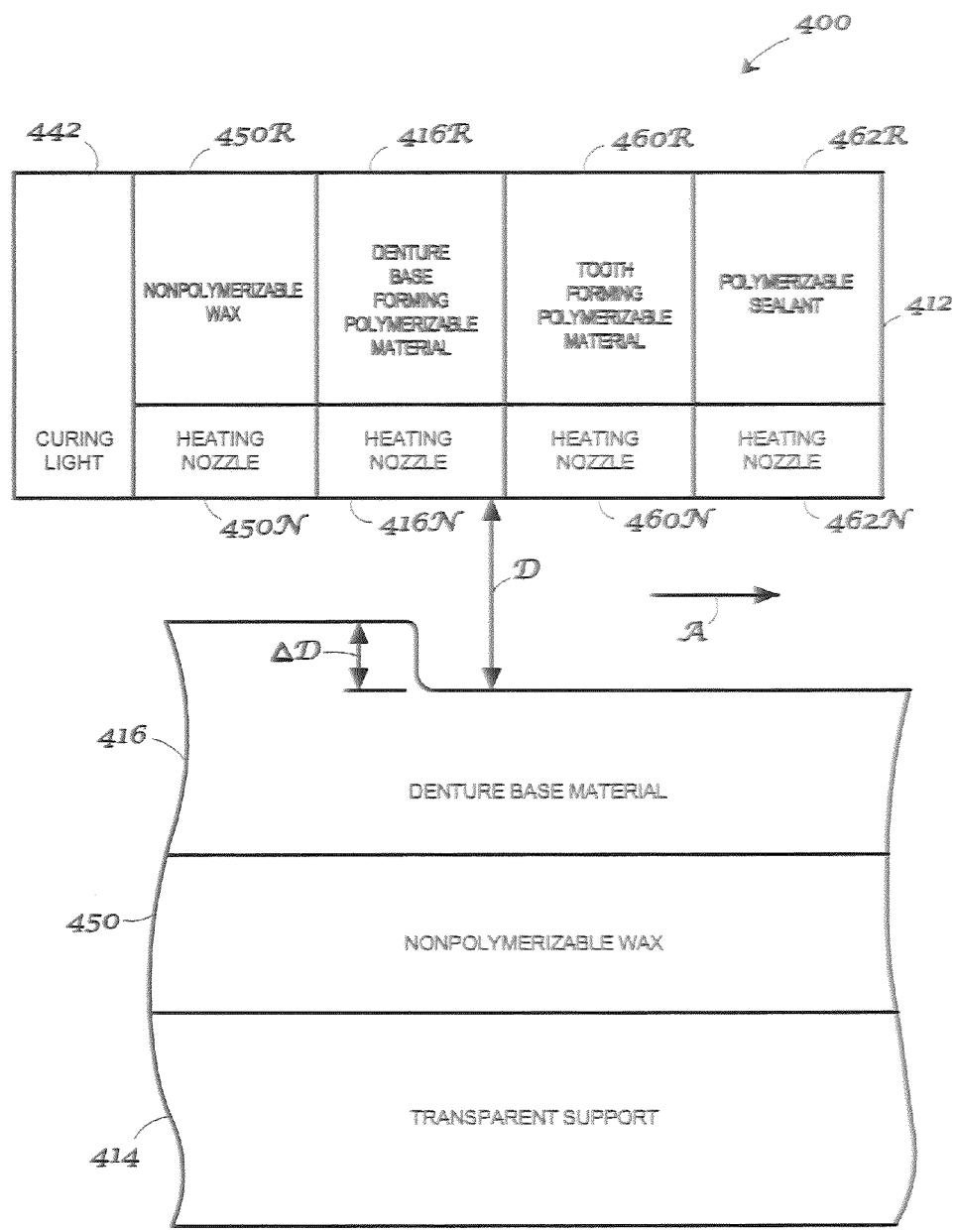
FIG. 7 is a schematic representation of a spray head forming a device in accordance with the invention.

With more particular reference to FIG. 7 is seen a spray and curing head system 400 having spray and curing head 412. Spray and curing head 412 may be used in place of jet and curing system 312 in dental product making system 300. Transparent support 414 may be used in place support surface 314, in dental product making system 300.

As spray and curing head 412 is moved laterally in direction of arrow A, a spray of denture base forming polymerizable material from reservoir 416R is sprayed through heating nozzle 416N onto denture base material layer 416 forming an incremental depth delta D of polymerizable material. The added incremental depth of polymerizable material delta D is then light cured. Some of the light for curing is emitted from curing light 442. As the incremental depth (delta D) layer of polymerizable material is light cured it becomes integrally connected to polymeric denture base material layer 416. Denture base forming polymerizable material from reservoir 416R is formed by following the procedure of Preparation 3 below.

Polymeric denture base material 416 is supported by nonpolymerizable wax layer 450. Nonpolymerizable wax layer 450 is formed by spraying nonpolymerizable wax from reservoir 450R through heating nozzle 450N onto transparent support 414. Nonpolymerizable wax layer 450 serves as a scaffold for polymeric denture base material layer 416.

In the upper portion of polymeric denture base material layer 416 sections of denture base forming polymerizable material from reservoir 416R are replaced by tooth forming polymerizable material sprayed from reservoir 460R is through heating nozzle 460N onto the adjacent portion of layer 416. This forms an incremental depth delta D of polymerizable material having sections of tooth forming polymerizable material in the layer of denture base forming polymerizable material. The added incremental depth of polymerizable material delta D is then light cured. Tooth forming polymerizable material sprayed from reservoir 460R is formed by following the procedure of Preparation 6 below.

Above the polymeric denture base material layer 416 only the sections of tooth forming polymerizable material continue to be sprayed from reservoir 460R is through heating nozzle 460N to incrementally form teeth. Each incremental depth delta D of polymerizable material in the sections of tooth forming polymerizable material incrementally form teeth above the layer of denture base forming polymerizable material. These added incremental depths of polymerizable material delta D are light cured. Over the polymeric denture base material layer 416 and over outer layer of each section of each tooth polymerizable sealant is sprayed from reservoir 462R through heating nozzle 462N to incrementally form sealed teeth and seal denture base.

Thus, a denture is formed in accordance with a preferred embodiment of the invention by, incrementally providing polymerizable material in the shape of a denture having a denture base and artificial teeth, and curing the polymerizable material to form a polymeric denture wherein the denture base and artificial teeth are integrally connected. So, a denture is formed in accordance with the invention for example by spraying liquid polymerizable material at between 60 and 80° C. into the shape of a denture having a denture base and artificial teeth, and curing the polymerizable material during and after solidifying and cooling to ambient temperature (about 23° C.), to form a polymeric denture. The polymerizable material sprayed is preferably in the form of a focused jet sprayed from a container. Preferably a family of containers is provided each having polymerizable material with a different shade of color. Some of the containers have shades of color for denture base. Others have shades of color for forming artificial teeth. These may include filler.

Location identifying markers may be placed in the patient's mouth and/or on a cast of the patient's mouth. The markers may be used to vary the thickness of the denture base.

In a preferred embodiment a first layer of deposit dots is built up and polymerized, followed by second layer is built up and polymerized followed by subsequent layers to form a dental prosthesis. Preferred dental prostheses are teeth and dentures having integrally formed teeth and denture base.

Preferably a plurality of containers each enclosing a liquid (or readily liquifiable) pigmented photopolymerizable (light curable) material having a color (or shade) different from the color (or shade) of the material in the other containers. A plurality of colors of material are combined to control the shade the denture base and each tooth of a denture formed in accordance with the invention. Information about the color of a patient's teeth (or skin) may be used to select a color of teeth to be formed in a partial or full denture for the patient in accordance with the invention.

In a preferred embodiment of the invention a denture is made by collecting digital information regarding a mouth, and forming a denture using the information. The digital information regarding a mouth may be collected at a first location, and the denture formed at a second location using the information. Polymerizable material is used to form the shape of a denture base and artificial teeth of the denture. The polymerizable material is cured to form a polymeric denture wherein the denture base and artificial teeth are integrally connected. The polymerizable material is sprayed into the shape of the denture having a denture base and artificial teeth, before curing the polymerizable material to form the polymeric denture.

In a preferred embodiment of the invention computer-control is used to rapidly manufacture dental devices by dispensing a first liquid wax-like polymerizable material at a first set of selected locations of a target surface. The first wax-like polymerizable material is polymerized to form at least a portion of a first polymeric layer of the dental device. The second liquid wax-like polymerizable material is dispensed at a second set of selected locations of a target surface. The second wax-like polymerizable material is polymerized to form at least a portion of a second polymeric layer of the dental device. The liquid wax-like polymerizable material may be dispensed by spraying. Preferably the first wax-like polymerizable material has a first color and said second wax-like polymerizable material has a second color. Additional layers are dispensed and polymerized to complete a dental device.

In a preferred embodiment of the invention provides a process for producing a three-dimensional object from a computer data base, comprising the steps of: dispensing and polymerizing layers of wax-like polymerizable material at controlled locations to form a three-dimensional object. Preferably, at least one of said layers of wax-like polymerizable material is effectively different from another of said layers of wax-like polymerizable material in a characteristic selected from the group consisting of color, texture and composition.

A preferred embodiment of the invention provides a denture by collecting digital information regarding a mouth, and forming a denture using the information. The collection of digital information regarding a mouth may be at a first location, and the formation a denture using the information may be at a second location. Preferably the digital information is the transferred from the first location to the second location through a telephone system, or while being stored on a disk that is transferred from the first location to the second location.

A preferred embodiment of the invention provides a denture by providing polymerizable material in the shape of a denture having a denture base and artificial teeth, and curing the polymerizable material to form a polymeric denture wherein the denture base and artificial teeth are integrally connected. This may be done by spraying polymerizable material into the shape of a denture having a denture base and artificial teeth, and curing the polymerizable material to form a polymeric denture.

In the following examples, unless otherwise indicated, all parts and percentages are by weight; Lucirin TPO refers to 2,4,6-trimethylbenzoyldiphenylphosphine oxide made by BASF, and the visible light curing unit used was an Eclipse visible light curing unit, sold by Dentsply International, providing about 30 milliwatts/cm$^2$ of from 350 to 450 nm light.

Preparation 1

Preparation of Oligomer

A reactor was charged with 1176 grams of trimethyl-1,6-diisocyanato-hexane (5.59 mol) and 1064 grams of bisphenol A propoxylate (3.09 mol) under dry nitrogen flow and heated to about 65° C. under a positive nitrogen pressure. To this reaction mixture, 10 drops of catalyst dibutyltin dilaurate were added. The temperature of the reaction mixture was maintained between 65° C. and 140° C. for about 70 minutes and followed by additional 10 drops of catalyst dibutyltin dilaurate. A viscous paste-like isocyanate end-capped intermediate product was formed and stirred for 100 minutes.

To this intermediate product, 662 grams (5.09 mol) of 2-hydroxyethyl methacrylate and 7.0 grams of BHT as an inhibitor were added over a period of 70 minutes while the reaction temperature was maintained between 68° C. and 90° C. After about five hours stirring under 70° C., the heat was turned off, and oligomer was collected from the reactor as semi-translucent flexible solid and stored in a dry atmosphere.

Preparation 2

Preparation of Monomer

A reaction flask was charged with 700 grams of 1,6-diisocyanatohexane and heated to about 70° C. under a positive nitrogen pressure. To this reactor were added 1027 grams of 2-hydroxyethyl methacrylate, 0.75 gram of catalyst dibutyltin dilaurate and 4.5 grams of butylated hydroxy toluene (BHT). The addition was slow and under dry nitrogen flow over a period of two hours. The temperature of the reaction mixture was maintained between 70° C. and 90° C. for another two hours and followed by the addition of 8.5 grams of purified water. One hour later, the reaction product was discharged as clear liquid into plastic containers and cooled to form a white solid and stored in a dry atmosphere.

Preparation 3
Preparation of Polymerizable Denture Base Plate Material

A light curable polymerizable material was prepared by stirring at 85° C. a liquid of 98.0 grams of TBDMA oligomer of Preparation 1, 0.35 gram of 2,4,6-trimethylbenzoyldiphenylphosphine oxide, (Lucirin TPO made by BASF), 1.5 gram of solution containing 8.3% camphorquinone (CQ), 25% ethyl 4-dimethylaminobenzoate (EDAB) and 66.7% 1,6-hexanediol dimethacrylate (HDDMA), 0.1 gram of red acetate fibers and 0.05 gram of pigment.

Preparation 4
Preparation of Polymerizable Wax-Like Denture Contour Material

A light curable wax-like polymerizable dental material was prepared by stirring at 85° C. a liquid mixture of 50.5 grams of oligomer of Preparation 1, 45.0 grams of monomer of Preparation 2 and 4.0 grams of stearyl acrylate from Sartomer. To this mixture were added 0.35 gram of 2,4,6-trimethylbenzoyldiphenylphosphine oxide (Lucirin TPO), 0.1 gram of red acetate fibers and 0.05 gram of pigment concentrates. The polymerizable wax-like material formed becomes flowable at 65 to 68° C.

Preparation 5
Preparation of Polymerizable Denture Set-Up Material

A light curable polymerizable material was prepared by stirring at 85° C. a liquid mixture of 84.5 grams of oligomer of Preparation 1 and 15.0 grams of monomer of Preparation 2. To this mixture, 0.35 gram of 2,4,6-trimethylbenzoyldiphenylphosphine oxide (Lucirin TPO), 0.1 gram of red acetate fibers and 0.05 gram of pigment were added.

Preparation 6
Preparation of Polymerizable Wax-Like Artificial Tooth Resin

A light curable wax-like polymerizable dental material was prepared by stirring at 85° C. a liquid mixture of 50 grams of oligomer of Preparation 1, 30.0 grams of monomer of Preparation 2 and 20 grams of monomer of Preparation 2. To this mixture were added 0.35 gram of 2,4,6-trimethylbenzoyldiphenylphosphine oxide (Lucirin TPO), and 0.05 gram of pigment concentrates. The polymerizable wax-like material formed becomes flowable at 65 to 70° C.

Preparation 7
Preparation of Monomer

A reaction flask was charged with 168 grams of 1,6-diisocyanatohexane and heated to about 70° C. under a positive nitrogen pressure. To this reactor were added 228 grams of 2-hydroxyethyl acrylate, 0.12 gram of catalyst dibutyltin dilaurate and 0.86 grams of butylated hydroxy toluene (BHT). The addition was slow and under dry nitrogen flow over a period of two hours. The temperature of the reaction mixture was maintained between 70° C. and 85° C. for another three hours and followed by the addition of 0.9 grams of purified water. One hour later, the reaction product was discharged as clear liquid into plastic containers and cooled to form a white solid and stored in a dry atmosphere.

Preparation 8
Preparation of Monomer

A reaction flask was charged with 47.7 grams of p-tolyl isocyanate and heated to about 46° C. under a positive nitrogen pressure. To this reactor were added 48.13 grams of 2-hydroxyethy methacrylate, 0.06 gram of catalyst dibutyltin dilaurate and 0.30 grams of butylated hydroxy toluene (BHT). The addition was under dry nitrogen flow over a period of 40 minutes while the temperature of the reaction mixture was raised to 78° C. and maintained between 72° C. and 78° C. for another 1.3 hours. The reaction product was discharged as clear liquid into a plastic container and cooled to form a semi-opaque off white solid and stored in a dry atmosphere.

EXAMPLES 1A AND 1B

Table 1 shows the components and Table 2 shows the properties of the compositions of Examples 1A through 1B. The compositions of Examples 1A through 1B were prepared by mixing the components shown in Table 1 at 95° C.

TABLE 1

| | Example 1A (grams) | Example 1B (grams) |
|---|---|---|
| Titanium dioxide | 0.385 | 0 |
| Iron oxide | 0.0499 | 0.002 |
| Red-Brown Pigment Blend | 0.0132 | 0.0012 |
| Ultramarine Blue Pigment | 0 | 0.0028 |
| Black Dry Color Blend | 0.0134 | 0 |
| a blend of 82.99% ZnO, 16.18% Magnesium carbonate, 0.62% Lithium sulfate and 0.21% Sulfur, (sublimed powder). [115 Phosphor] | 0.194 | 0.05 |
| dihydroxy terepthalate acid ester [FLU-L-BLU] | 0.08 | 0.024 |
| Monomer of Preparation 2 | 40.4 | 17.2 |
| Monomer of Preparation 7 | 28.0 | 24.6 |
| Monomer of Preparation 8 | | 24.6 |
| Oligomer of Preparation 1 | 68.16 | 41.6 |
| Lucirin TPO | 0.6 | 0.32 |
| Camphorquinone | 0.32 | 0.212 |
| N,N-dimethyl-aminoneopentyl acrylate | 1.11 | 0.74 |
| Methacrylic Acid | 0.55 | 0.368 |
| Butylated Hydroxytoluene | 0.03 | 0.02 |
| γ-methacryloxypropyl-silane | 0.39 | 0.26 |
| silanated fumed silica*** ($SiO_2$) | 28.54 | 6 |
| silanated barium aluminoflurosilicate glass (BAFG)** | 228.39 | 168 |
| silanated barium aluminoflurosilicate glass (BAFG)* | 114.19 | 116 |

*Barium glass particles having an average particle size of from about 1 to about 10 micrometers.
**Barium glass particles having an average particle size of from about 0.1 to about 1 micrometers.
***Fumed silica having an average particles size of from about 0.01 to about 0.04 micrometers.

The physical properties of the material of Examples 1A and 1B were tested and results listed in Table 2:

TABLE 2

| Property | Example 1A | Example 1B |
|---|---|---|
| Localized Wear - $mm^3$ | 0.021 | |
| Flexural Strength - psi | 19,600 | 17,330 |
| Flexural Modulus - kpsi | 1,625 | 1,580 |
| Compressive Strength - MPa | 358** | |
| Water Sorption - $\mu g/mm^3$ | 14.9 | |

**Compressive Strength was measured using 50 kN load cell set to run at 2,000 pounds with crosshead speed at 2 inches (50.8 mm)/per minute. Compressive strength testing specimens were prepared by following the procedure of U.S. Pat. No. 6,387,981. Each composite was packed into a 4 mm inside diameter glass tube, capped with silicone rubber plugs and axially compressed at about 0.28 MPa for 15 minutes, then light cured for 10 minutes in Eclipse light curing unit (voltage at 37.5 V, blowers at 80 percent). Cured samples were cut on a diamond saw to form cylindrical plugs 8 mm long and stored in distilled water at 37° C. for 24 hours and then measured for compressive strength.

A three body cyclic abrasion wear machine (Leinfelder/ University of Alabama in vitro) was used to determine volume loss (cubic mm at 400,000 cycles), as a measure of the wear resistance of the polymerized composite compositions of Examples 1A and 1B.

Water sorption of the polymerized composite compositions of Examples 1A and 1B was measured according to ISO 4049. The samples were cured for 10 minutes in the Eclipse light curing unit (voltage at 37.5 V, blowers at 80% from 5:30-10:00 minutes). Flexural Strength and Flexural Modulus of the polymerized composite compositions of Examples 1A and 1B were measured by using three-point bend test on Instron bending unit according to ASTM D790 (1997). Samples were cured in metal molds in an Eclipse light curing unit for 10 minutes (voltage at 37.5 V, blowers at 80% from 5.5-10 minutes).

EXAMPLE 2

Continuous Tooth Making

Two steel disks each has a cylindrical outer face with a sequence of tooth mold halves therein. The two steel disks are rotated so that they are in contact along their outer cylindrical faces. The corresponding tooth mold halves on each disk are aligned while their portions of the cylindrical outer faces are in the contact. A sheet of polymerizable wax-like material at 60° C., formed by following the procedure of Preparation 6, is continuously fed between the aligning outer faces of the two rotating steel disks, each at 37° C. The corresponding tooth mold halves on each disk shape 0.5 g to 2 g portions of the polymerizable wax-like material into artificial teeth as they rotate into alignment with each other.

EXAMPLE 3

Multiple Layered Tooth Making

Each of two steel mold halves has fourteen half tooth molds therein. The two steel mold halves (each at 37° C.) are positioned in contact, with the corresponding half tooth molds aligned, and a sheet of polymerizable wax-like composite material (at 60° C.) positioned between the aligned faces of the two mold halves. The polymerizable wax-like composite material is formed by following the procedure of Example 1B. The corresponding tooth mold halves shape 0.3 g portions of the polymerizable wax-like composite material into each of the enamels of artificial teeth as they are aligned with each other. One steel mold half (without enamels of artificial teeth) is removed and an additional steel mold half (at 37° C.) applied in its place, so that the mold halves are in contact along their mold outer faces. The additional steel mold also has fourteen half tooth molds therein. A sheet of polymerizable wax-like composite material at 60° C., formed by following the procedure of Example 1A, is positioned between the two mold halves. The polymerizable wax-like composite material is forced into the tooth mold cavities. The corresponding tooth mold halves shape 1 g portions of the polymerizable wax-like composite material (at 60° C.) into each of the artificial tooth bodies. Each artificial tooth body combines with the enamel in its mold cavity to form a two layer artificial tooth.

The fourteen teeth formed are positioned into a molded denture base of material prepared by following the procedure of Preparation 3, and light cured by impinging light thereon for 60 seconds from a Spectrum 800 light curing unit (sold by Dentsply International Inc), followed by curing for 10 minutes in a Triad 2000 light curing unit (sold by Dentsply International Inc). The adjacent surfaces of the teeth and the denture base combine during polymerization to form an integral denture.

EXAMPLE 4

Continuous Multiple Layered Tooth Making

Each of two steel disks has a sequence of fourteen half teeth molds in its cylindrical outer face. The two steel disks (each at 37° C.) are rotated so that they are in contact along their outer cylindrical faces, with the corresponding half tooth molds aligned, as a sheet of polymerizable wax-like composite material (at 60° C.) continuously fed between the aligned faces of the two disks. The polymerizable wax-like composite material is formed by following the procedure of Example 1B. The corresponding tooth mold halves shape 0.3 g portions of the polymerizable wax-like composite material into each of the enamels of artificial teeth as they are rotated into alignment with each other. One steel disk without enamels of artificial teeth is removed and an additional steel disk (at 37° C.) put in its place, so that the mold halves are in contact along their mold outer faces as they are rotated. The additional steel disk also has fourteen half tooth molds therein. A sheet of polymerizable wax-like composite material at 60° C., formed by following the procedure of Example 1A, is continuously fed between the two disks. The polymerizable wax-like composite material is forced into the tooth mold cavities. The corresponding tooth mold halves shape 1 g portions of the polymerizable wax-like composite material (at 60° C.) into artificial tooth bodies. Each artificial tooth body combines with the enamel in its mold cavity to form a two layer artificial tooth.

The fourteen teeth formed are positioned into a molded denture base of material prepared by following the procedure of Preparation 4, and light cured by impinging light thereon for 10 minutes in an Eclipse light curing unit, sold by Dentsply International Inc. The adjacent surfaces of the teeth and the denture base combine during polymerization to form an integral denture.

EXAMPLE 5

Preparation of a Denture without Forming a Mold Cavity of a Denture Base

A plaster cast of a patient's mouth is coated with a release agent (e.g., Al-Cote and Isolant sold by Dentsply International Inc. or Teflon solution such as Krytox from Dupont) and heated to 55° C. in an incubator. An arch-shaped baseplate resin containing 14 grams of the product of Preparation 3 is applied and shaped onto the warm cast. The resin is shaped and flowed to fully cover the cast, using finger pressure and trimming to form a baseplate. The baseplate is cured for 10 minutes in the visible light curing unit. A sufficient quantity of the product of Preparation 5 is formed into a rope. The rope is applied to the baseplate. Artificial teeth formed by following the procedure of Example 3 are then pressed into the rope with the thickness of the rope adapted to adequately cover the appropriate surfaces of the teeth to provide support. Melted product of Preparation 4 from an about 87° C. wax pot is applied by using an electric spatula between the teeth and the baseplate to fully embed teeth and to flow into fissures between teeth and to smooth the outer surface of the denture. Hot air from a small nozzle hot air gun may also be applied to let the product of Preparation 4 flow into fissures between teeth and smooth the outer surface of the denture. The lingual and buccal surfaces of the denture are contoured, trimmed and carved using a spatula. The denture is placed in a patient's mouth for try-in at a dental office, the tooth positions are adjusted. The uncured teeth are carved, trimmed, melted and softened to adjust their horizontal and vertical positions and shapes. The denture back (tissue side) is filled with fresh plaster and allowed to set. TRIAD Air Barrier Coating is painted on the dentureand cured in an Eclipse visible light curing unit (sold by Dentsply International) for 10 minutes. The artificial teeth are integrally connected to the denture base. When cured, the denture is washed with water to remove all traces of Air Barrier Coating. The denture is then finished and polished.

EXAMPLE 6

Preparation of Oligomer

A reactor was charged with 150 grams of 1,6-diisocyanatohexane and 200 grams of bisphenol A propoxylate under dry nitrogen flow and heated to about 56° C. under positive nitrogen pressure. To this reaction mixture, 0.12 gram of catalyst dibutyltin dilaurate was added. The temperature of the reaction mixture was maintained between 65° C. and 80° C. for about 3.5 hours. To this isocyanate end-capped intermediate product, 82.96 grams of 2-hydroxyethyl methacrylate and 2.15 grams of BHT as an inhibitor were added over a period of 50 minutes while the reaction temperature was maintained between 55° C. and 75° C. After about five hours stirring, the heat was turned off, and oligomer was collected from the reactor as semi-translucent flexible solid and stored in a dry atmosphere.

Preparation of Wax-Like Spray Tooth Making Material

Wax-like Spray Tooth Making Material is formed by mixing the at from 85° C. 29.5 g oligomer made by following the above procedure of this example (for Preparation of Oligomer), 19.7 g Cyclohexane dimethanol diacrylate, 1.4 g Shading Pigments, 0.1 percent camphorquinone, 0.1 g 2,4,6-trimethylbenzoyl-diphenylphosphine oxide, 18.6 g silanated barium aluminoflurosilicate glass (BaBFAlSiO$_4$): a mean particle size from 4 to 7 (micron) and a maximum particle size of 50 (micron), 26.7 g silanated barium aluminoflurosilicate glass (BaBFAlSiO$_4$): a mean particle size of 0.92-0.96 (micron) and a maximum particle size of 3.75 (micron), 3.9 g silanated fumed silica (SiO$_2$). The polymerized product has 0.013 mm$^3$ wear volume loss at 400,000 cycles. The cooled material is then light cured by impinging light thereon for 30 seconds from a light curing unit (Spectrum 800 sold by Dentsply International Inc).

It should be understood that while the present invention has been described in considerable detail with respect to certain specific embodiments thereof, it should not be considered limited to such embodiments but may be used in other ways without departure from the spirit of the invention and the scope of the appended claims.

What is claimed is:

1. A method for making a three-dimensional dental prosthesis, comprising the steps of:
   a) collecting digital information for making the prosthesis;
   b) providing an ink-jet printer having:
      i) a ink-jet sprayer;
      ii) a curing head;
      iii) at least one reservoir with a first light-curable wax-like polymerizable material; and
      iv) at least one reservoir with a nonpolymerizable wax material;
   c) applying one or more layers of the nonpolymerizable wax material onto a support surface to form a scaffold for the first light-curable wax-like polymerizable material;
   d) applying layers of the light-curable wax-like polymerizable material onto the one or more layers of the nonpolymerizable wax material to form a multi-layered, uncured dental prosthesis, each layer being formed by the ink-jet sprayer spraying the first material through a heating nozzle onto the nonpolymerizable wax material according to the digital information, the first material comprising a mixture of monomer, oligomer, and light sensitizer and being dimensionally stable in its uncured state at ambient temperature; and
   e) moving the curing head in the direction of the ink-jet sprayer to cure a sprayed first material thereby light-curing at least a portion of the prosthesis so that it cures to form a polymerized prosthesis made of a polymeric matrix, which alone, has a flexural modulus of at least 250,000 psi and a flexural strength of at least 5,000 psi.

2. The method of claim 1, wherein the digital information is collected and a digital model is produced by scanning a portion of the patient's mouth or by scanning a hardened dental impression of the patient's mouth.

3. The method of claim 1, wherein the light sensitizer is selected from the group consisting of camphorquinone; 2,4,6 trimethylbenzoyldiphenyl phosphine oxide (TPO); and ethyl (4-N, N-dimethylamino) benzoate.

4. The method of claim 1, wherein the wax-like polymerizable material further comprises reinforcing filler.

5. The method of claim 1, wherein the wax-like polymerizable material further comprises pigment.

6. The method of claim 1, wherein at least two layers of wax-like polymerizable material are applied onto the support surface to form the prosthesis.

7. The method of claim 1, wherein at least two layers of wax-like polymerizable material are applied onto the support surface to form the prosthesis and at least two of the layers are of different colored shades.

8. The method of claim 1, wherein at least two layers of wax-like polymerizable material are applied onto the support surface to form the prosthesis and at least two of the layers have different compositions.

9. The method of claim 1, wherein the device is made of a polymeric matrix, which alone, has a flexural modulus of at least 300,000 psi and a flexural strength of at least 7,000 psi.

10. The method of claim 1, wherein the prosthesis is selected from the group consisting of a dental bridge, full denture, or partial denture.

11. A method for making a three-dimensional integrated denture having artificial teeth, comprising the steps of:
   a) collecting digital information for making the denture;
   b) providing an ink-jet printer including:
      i) a jet and curing system having:
         aa) at least one ink-jet sprayer; and
         bb) a curing head;
      ii) a first reservoir with a first light-curable wax-like polymerizable material;
      iii) a second reservoir with a second light-curable wax-like polymerizable material that has a different composition than the first light-curable wax-like polymerizable material; and
      iv) a third reservoir with a nonpolymerizable wax material;
   c) applying one or more layers of the nonpolymerizable wax material from a third ink-jet sprayer through a third heating nozzle onto a support surface to form a scaffold for first light-curable wax-like polymerizable material;
   d) applying multiple layers of the first light-curable wax-like polymerizable material onto the nonpolymerizable wax material to form a multi-layered, uncured denture base, each layer being formed by a first ink-jet sprayer spraying the first material through a first heating nozzle according to the digital information, the first wax-like material comprising a mixture of monomer, oligomer, and light sensitizer and being dimensionally stable in its uncured state at ambient temperature;

e) applying the second light-curable wax-like polymerizable material from a second ink-jet sprayer through a second heating nozzle in the form of artificial teeth to the denture base to form an integrated denture, the second wax-like material comprising a mixture of monomer, oligomer, and light sensitizer and being dimensionally stable in its uncured state at ambient temperature; and f) light-curing the denture base and artificial teeth together to form a polymerized integrated denture made of a polymeric matrix, which alone, has a flexural modulus of at least 250,000 psi and a flexural strength of at least 5,000 psi.

12. The method of claim 11, wherein the digital information is collected and a digital model is produced by scanning a portion of the patient's mouth or by scanning a hardened dental impression of the patient's mouth.

13. The method of claim 11, wherein the first and second wax-like polymerizable materials each comprises reinforcing filler.

14. The method of claim 11, wherein the first and second wax-like polymerizable material each comprises pigment.

15. The method of claim 11, wherein the first and second wax-like polymerizable material have different colored shades.

16. The method of claim 11, wherein the ink-sprayer and curing head are located on an ink and curing head that is moved laterally in a predetermined direction so that a spray first material from the first reservoir is sprayed through the heating nozzle onto a deposited first material layer forming an added first material layer having an incremental depth delta D of the first material and wherein the added incremental depth of the first material delta D is then light cured.

17. The method of claim 16, wherein above the added first material layer, sections or layers of the second material are sprayed from the second reservoir through the second heating nozzle to incrementally form teeth such that each incremental depth delta D of the second material in the sections or layers of tooth forming second material incrementally form teeth above a cured added layer of first material that forms at least a portion of the denture base and wherein these added incremental depths of the second material delta D are light cured.

18. The method of claim 11, wherein the jet and curing system is incrementally moved in a plane above the support surface by at least one horizontal actuator such that for each increment the jet and curing system is moved in a plane above the support surface, the jet and curing system is moved laterally across at least a portion of support surface by at least one lateral actuator.

19. The method of claim 18, wherein after the jet and curing system is incrementally moved through at least a portion of a plane above the support surface by the at least one horizontal actuator, at least one vertical actuator lowers the support surface and the at least one horizontal actuator a distance corresponding to a height of an added layer of the first material, the second material, or both sprayed and polymerized.

20. The method of claim 11, wherein
the ink-jet printer further includes a fourth reservoir with a polymerizable sealant; and
the method further comprises the step of spraying the polymerizable sealant from a forth ink-jet sprayer through a forth heating nozzle over portions of the first light-curable wax-like polymerizable material and second light-curable wax-like polymerizable material to form a seal.

* * * * *